United States Patent
Johnson et al.

(10) Patent No.: US 11,191,374 B1
(45) Date of Patent: Dec. 7, 2021

(54) AROMATHERAPY BLANKET ASSEMBLY

(71) Applicants: David Johnson, Marietta, GA (US);
Candace Johnson, Marietta, GA (US)

(72) Inventors: David Johnson, Marietta, GA (US);
Candace Johnson, Marietta, GA (US)

(*) Notice: Subject to any disclaimer, the term of this patent is extended or adjusted under 35 U.S.C. 154(b) by 0 days.

(21) Appl. No.: 17/024,098

(22) Filed: Sep. 17, 2020

(51) Int. Cl.
A61M 21/02 (2006.01)
A47G 9/00 (2006.01)
A47G 9/02 (2006.01)
A61M 21/00 (2006.01)

(52) U.S. Cl.
CPC ........... *A47G 9/007* (2013.01); *A47G 9/0223* (2013.01); *A61M 21/02* (2013.01); *A61M 2021/0016* (2013.01); *A61M 2205/3613* (2013.01)

(58) Field of Classification Search
CPC . A47G 9/00; A47G 9/02; A47G 9/007; A47G 9/0223; A61M 21/02
See application file for complete search history.

(56) References Cited

U.S. PATENT DOCUMENTS

| 4,005,499 | A | 2/1977 | Klein |
| 5,918,333 | A | 7/1999 | Takashima |
| 8,850,643 | B2 * | 10/2014 | White ............ A47G 9/007 5/641 |
| 2006/0272092 | A1 | 12/2006 | Tanner |
| 2007/0220674 | A1 | 9/2007 | Haskins |
| 2013/0013036 | A1 | 1/2013 | Zaragosa |
| 2014/0053338 | A1 * | 2/2014 | White ............ A47G 9/007 5/641 |

FOREIGN PATENT DOCUMENTS

CA 2868488 12/2014

* cited by examiner

*Primary Examiner* — Christine H Matthews

(57) ABSTRACT

An aromatherapy blanket assembly includes a blanket that is positionable on a user for warming the user. A panel is foldable onto itself to form a pouch and the panel is removably attachable to the blanket. A plurality of beads is positioned in the pouch formed by the panel and each of the beads is infused with a chemical scent to release the scent into the pouch. A plurality of infusion lines is integrated into the blanket. An infusion unit is removably attachable to the blanket such that the infusion unit is in fluid communication with the plurality of infusion lines. The infusion unit contains a liquid scent thereby facilitating each of the infusion lines to release the scent associated with the liquid scent from the blanket for the purposes of aromatherapy.

9 Claims, 5 Drawing Sheets

AROMATHERAPY BLANKET ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to aromatherapy device and more particularly pertains to a new aromatherapy device for releasing aromatherapy scents from a blanket.

(2) Description of Related Art Including Information Disclosed Under 37 CFR 1.97 and 1.98

The prior art relates to aromatherapy devices including a modular blanket assembly that can be quickly broken down into individual components. The prior art discloses a deodorizing pillow that includes pockets for containing odor absorbing materials. The prior art discloses a blanket with odor absorbing properties for absorbing odors from a user. The prior art discloses an aromatherapy heating pad that is wearable on a user for soothing joint pain while emitting a pleasing odor.

BRIEF SUMMARY OF THE INVENTION

An embodiment of the disclosure meets the needs presented above by generally comprising a blanket that is positionable on a user for warming the user. A panel is foldable onto itself to form a pouch and the panel is removably attachable to the blanket. A plurality of beads is positioned in the pouch formed by the panel and each of the beads is infused with a chemical scent to release the scent into the blanket. A plurality of infusion lines is integrated into the blanket. An infusion unit is removably attachable to the blanket such that the infusion unit is in fluid communication with the plurality of infusion lines. The infusion unit contains a liquid scent thereby facilitating each of the infusion lines to release the scent associated with the liquid scent from the blanket for the purposes of aromatherapy.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
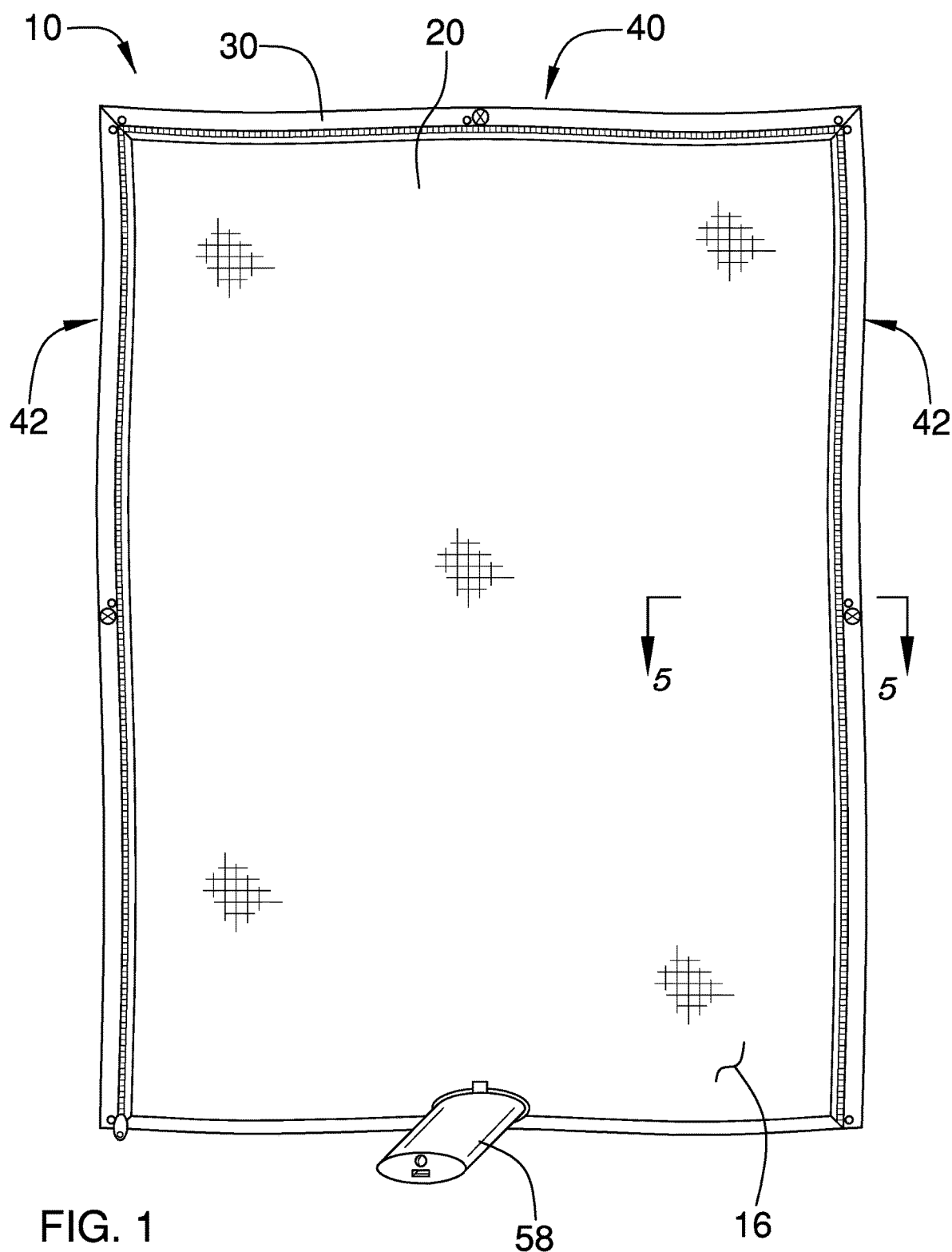
FIG. 1 is a top perspective view of an aromatherapy blanket assembly according to an embodiment of the disclosure.
Figure 2:
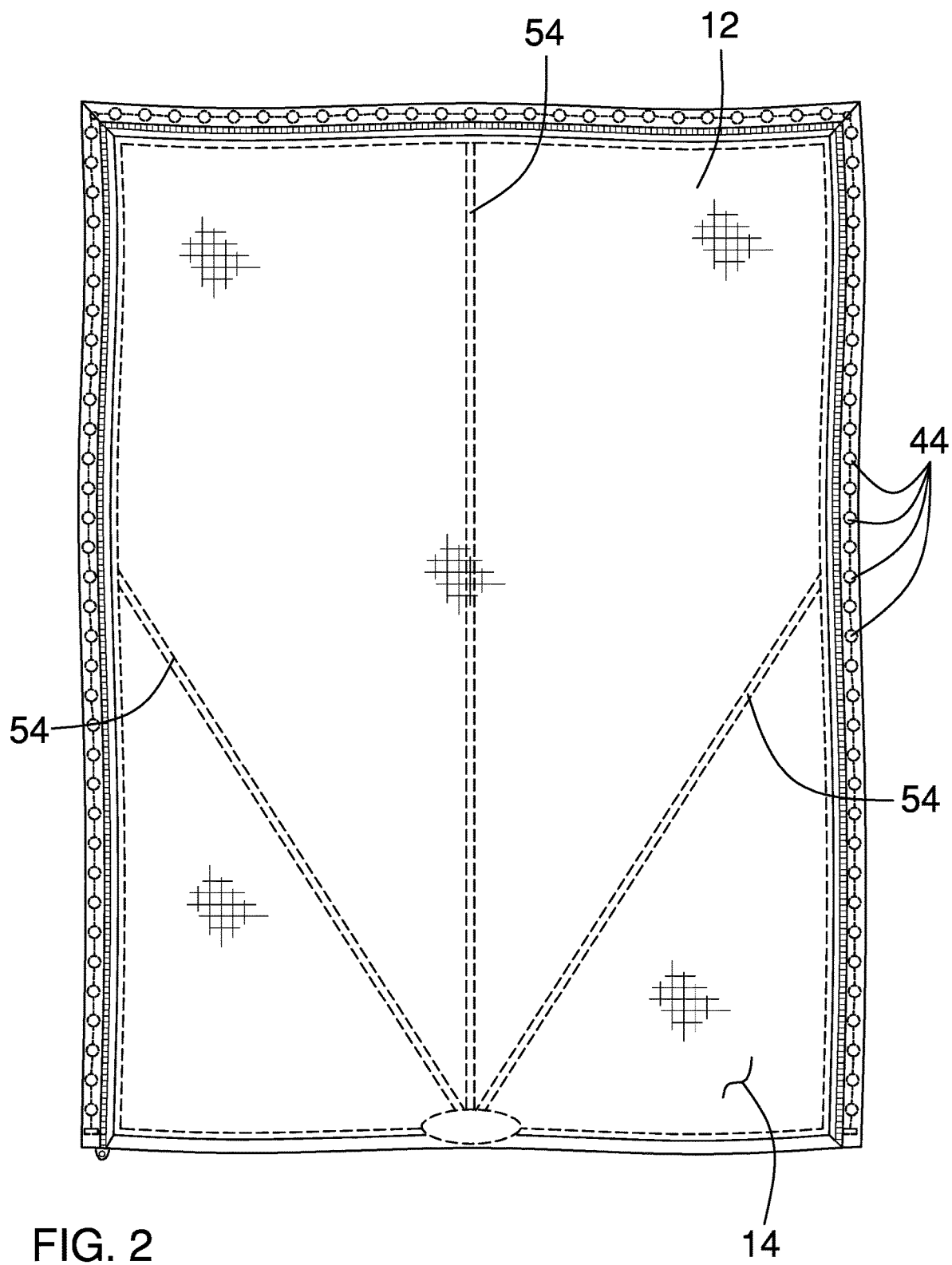
FIG. 2 is a bottom phantom view of an embodiment of the disclosure.
Figure 3:
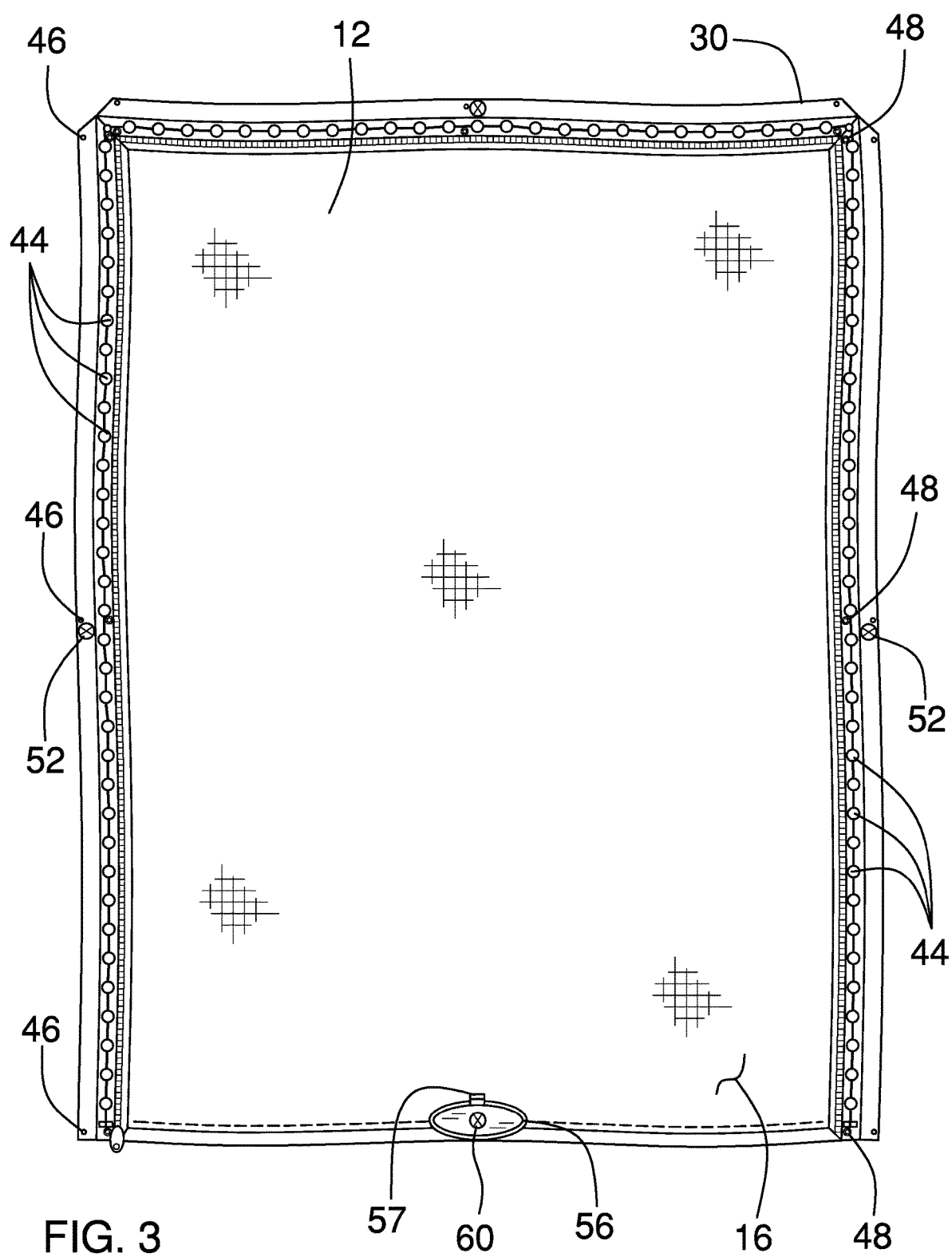
FIG. 3 is a top view of an embodiment of the disclosure.
Figure 4:
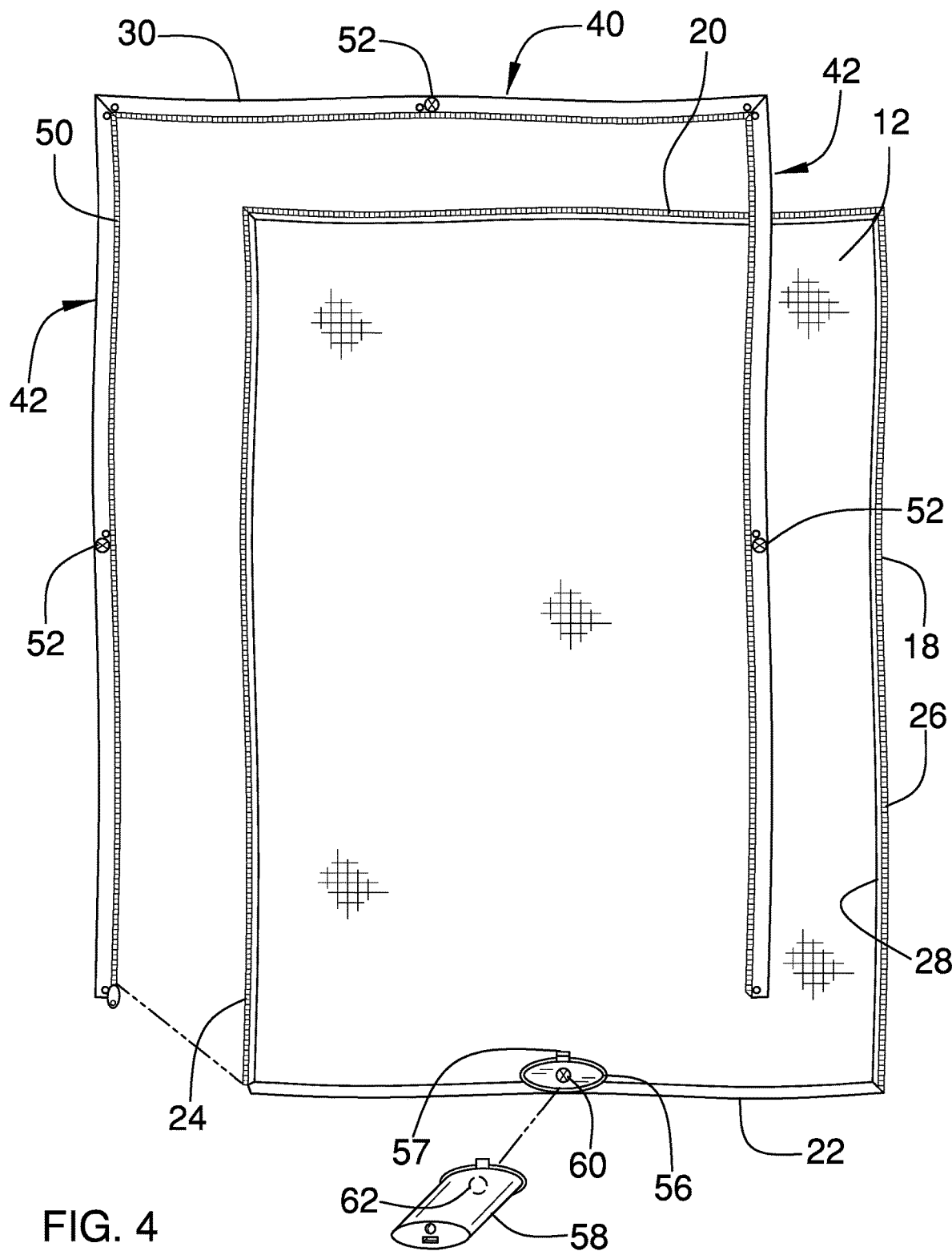
FIG. 4 is an exploded perspective view of an embodiment of the disclosure.
Figure 5:
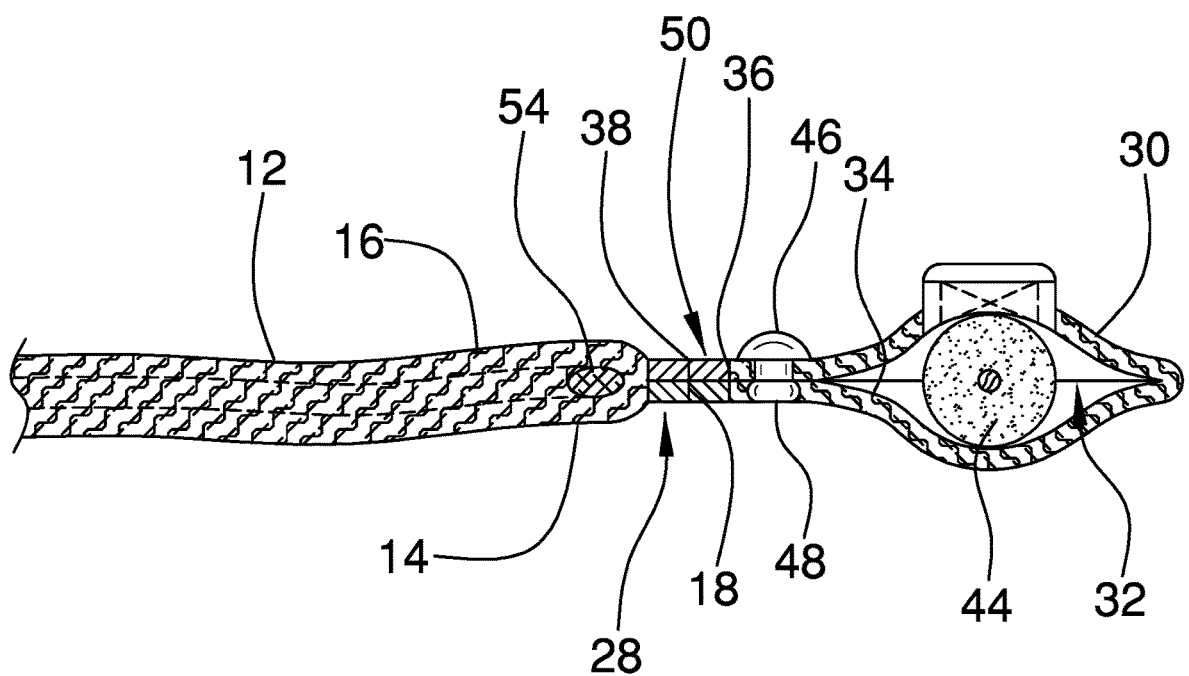
FIG. 5 is a cross sectional view taken along line 5-5 of FIG. 1 of an embodiment of the disclosure.

With reference now to the drawings, and in particular to FIGS. 1 through 5 thereof, a new aromatherapy device embodying the principles and concepts of an embodiment of the disclosure and generally designated by the reference numeral 10 will be described.

As best illustrated in FIGS. 1 through 5, the aromatherapy blanket assembly 10 generally comprises a blanket 12 that is positionable on a user to warm the user. The blanket 12 has a lower surface 14, a top surface 16 and a perimeter edge 18 extending therebetween, and the perimeter edge 18 has a back side 20, a front side 22, a first lateral side 24 and a second lateral side 26. Additionally, the blanket 12 is comprised of a fluid permeable material, including but not being limited to, an organic textile such as cotton or the like. A first mating member 28 is provided and the first mating member 28 is coupled to the blanket 12. The first mating member 28 extends along each of the first lateral side 24, the second lateral side 26 and the back side 20 of the perimeter edge 18 of the blanket 12.

A panel 30 is provided and the panel 30 is foldable onto itself to form a pouch 32. The panel 30 is removably attachable to the blanket 12 and the panel 30 has a bottom surface 34 extending between a back edge 36 and a front edge 38. Additionally, the back edge 36 is aligned with the front edge 38 and the bottom surface 34 rests against itself when the panel 30 is folded onto itself. The panel 30 includes a central portion 40 extending between a pair of outward portions 42, and each of the outward portions 42 is oriented perpendicular to the central portion 40 such that the panel 30 has a U shape.

A plurality of beads 44 is provided and each of the beads 44 is positioned in the pouch 32 formed by the panel 30. Each of the beads 44 is infused with a chemical scent to release the scent into the pouch 32. The beads 44 are distributed along each of the outward portions 42 and the central portion 40 of the panel 30. The chemical scent may be an essential oil or other type of volatile compound that is commonly associated with aromatherapy. Additionally, each of the beads 44 may be attached together to form a chain of the beads 44.

A plurality of first couplers 46 is each coupled to the panel 30. The first couplers 46 are spaced apart from each other and are distributed along the back edge 36 of the panel 30. A plurality of second couplers 48 is each coupled to the panel 30. Each of the second couplers 48 is spaced apart from each other and is distributed along the front edge 38 of the panel 30. Additionally, each of the second couplers 48 is aligned with a respective one of the first couplers 46. Each of the second couplers 48 releasably engages the respective first coupler 46 when the pouch 32 is folded onto itself thereby facilitating the pouch 32 to enclose the plurality of beads 44. Each of the first couplers 46 and the second couplers 48 may comprise a complementary portion of a snap or other type of releasable fastener.

A second mating member 50 is coupled to the panel 30 and the second mating member 50 releasably engages the first mating member 28 for attaching the panel 30 to the blanket 12. The second mating member 50 extends along a full length of the front edge 38 of the panel 30. A plurality of vents 52 is each coupled to the panel 30 to pass air into the pouch 32. In this way the vents 52 facilitate the beads 44 to release the chemical scent from the pouch 32 for the purposes of aromatherapy. Each of the vents 52 may be adjustable with respect to the volume of air allowed to pass through the vents 52.

A plurality of infusion lines 54 is each integrated into the blanket 12 and each of the infusion lines 54 is comprised of a fluid absorbent material. Each of the infusion lines 54 is positioned between the top surface 16 and the bottom surface 34 of the blanket 12. Additionally, the plurality of infusion lines 54 is arranged into an array in the blanket 12. An input 56 is coupled to the blanket 12 and the input 56 is in fluid communication with the plurality of infusion lines 54. The input 56 is positioned on the top surface 16 of the blanket 12 and the input 56 is positioned adjacent to the front side 22 of the perimeter edge 18 of the blanket 12. The input 56 may include an engagement 57 that is movably coupled thereto, and the engagement 57 may comprise a mechanical clip, a biased tab or any other type of releasable engagement.

An infusion unit 58 is provided that is removably attachable to the input 56 such that the infusion unit 58 is in fluid communication with the plurality of infusion lines 54. The engagement 57 may releasably engage the infusion unit 58 for retaining the infusion unit on the input 56. The infusion unit 58 contains a liquid scent thereby facilitating each of the infusion lines 54 to absorb the liquid scent. In this way the infusion lines 54 can release the scent associated with the liquid scent from the blanket 12 for the purposes of aromatherapy. The infusion unit 58 may comprise an electronic oil heater, an electronic potpourri heater or any other electronic device that can deliver the liquid scent to the infusion lines 54. The input 56 may have a fluid coupling 60 integrated therein that engages an output 62 of the infusion unit 58. In this way the infusion unit 58 can deliver the liquid scent to the infusion lines 54 for releasing the scent through the blanket 12. The liquid scent contained in the infusion unit 58 may be an essential oil or other volatile compound commonly associated with aromatherapy.

In use, each of the beads 44 is soaked with a liquid scent of preference and each of the beads 44 is enclosed in the pouch 32. The pouch 32 is attached to the blanket 12 and the infusion unit 58 is attached to the input 56 thereby facilitating the liquid scent in the infusion unit 58 to be absorbed into the infusion lines 54. In this way the beads 44 and the infusion lines 54 release the scent while the user is covered with the blanket 12. Thus, the blanket 12 keeps the user warm and comfortable while the user enjoys aromatherapy from the beads 44 and the infusion lines 54.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. An aromatherapy blanket assembly for releasing a therapeutic aroma while covering a user, said assembly comprising:

a blanket being positionable on a user wherein said blanket is configured to warm the user;

a panel being foldable onto itself to form a pouch, said panel being removably attachable to said blanket;

a plurality of beads, each of said beads being positioned in said pouch formed by said panel, each of said beads being infused with a chemical scent wherein each of said beads is configured to release the scent into said pouch;

a plurality of vents, each of said vents being coupled to said panel wherein each of said vents is configured to pass air into said pouch thereby facilitating said beads to release the chemical scent from said pouch for purposes of aromatherapy;

a plurality of infusion lines, each of said infusion lines being integrated into said blanket, each of said infusion lines being comprised of a fluid absorbent material;

an input being coupled to said blanket, said input being in fluid communication with said plurality of infusion lines; and an infusion unit being removably attachable to said input such that said infusion unit is in fluid communication with said plurality of infusion lines, said infusion unit containing a liquid scent thereby facilitating each of said infusion lines to absorb the liquid scent wherein said infusion lines are configured to release the scent associated with the liquid scent from said blanket for the purposes of aromatherapy.

2. The assembly according to claim 1, wherein:
said blanket has a lower surface, a top surface and a perimeter edge extending therebetween, said perimeter edge having a back side, a front side, a first lateral side and a second lateral side, said blanket being comprised of a fluid permeable material; and
said assembly includes a first mating member being coupled to said blanket, said first mating member extending along each of said first lateral side, said second lateral side and said back side of said perimeter edge of said blanket.

3. The assembly according to claim 2, wherein said panel has a bottom surface extending between a back edge and a front edge, said back edge being aligned with said front edge when said panel is folded onto itself, said panel including a central portion extending between a pair of outward portions, each of said outward portions being oriented perpendicular to said central portion such that said panel has a U shape.

4. The assembly according to claim 3, wherein said beads are distributed along each of said outward portions and said central portion of said panel.

5. The assembly according to claim 3, further comprising a plurality of first couplers, each of said first couplers being coupled to said panel, said first couplers being spaced apart from each other and being distributed along said back edge of said panel.

6. The assembly according to claim 5, further comprising a plurality of second couplers, each of said second couplers being coupled to said panel, each of said second couplers being spaced apart from each other and being distributed along said front edge of said panel, each of said second couplers being aligned with a respective one of said first couplers, each of said second couplers releasably engaging said respective first coupler when said pouch is folded onto itself thereby facilitating said pouch to enclose said plurality of beads.

7. The assembly according to claim 2, further comprising a second mating member being coupled to said panel, said second mating member releasably engaging said first mating member for attaching said panel to said blanket, said second mating member extending along a full length of a front edge of said panel.

8. The assembly according to claim 2, wherein:
each of said infusion lines is positioned between said top surface and said lower surface of said blanket, said plurality of infusion lines being arranged into an array in said blanket; and
said input is positioned on said top surface of said blanket, said input being positioned adjacent to said front side of said perimeter edge of said blanket.

9. An aromatherapy blanket assembly for releasing a therapeutic aroma while covering a user, said assembly comprising:
a blanket being positionable on a user wherein said blanket is configured to warm the user, said blanket having a lower surface, a top surface and a perimeter edge extending therebetween, said perimeter edge having a back side, a front side, a first lateral side and a second lateral side, said blanket being comprised of a fluid permeable material;
a first mating member being coupled to said blanket, said first mating member extending along each of said first lateral side, said second lateral side and said back side of said perimeter edge of said blanket;
a panel being foldable onto itself to form a pouch, said panel being removably attachable to said blanket, said panel having a bottom surface extending between a back edge and a front edge, said back edge being aligned with said front edge when said panel is folded onto itself, said panel including a central portion extending between a pair of outward portions, each of said outward portions being oriented perpendicular to said central portion such that said panel has a U shape;
a plurality of beads, each of said beads being positioned in said pouch formed by said panel, each of said beads being infused with a chemical scent wherein each of said beads is configured to release the scent into said pouch, said beads being distributed along each of said outward portions and said central portion of said panel;
a plurality of first couplers, each of said first couplers being coupled to said panel, said first couplers being spaced apart from each other and being distributed along said back edge of said panel;
a plurality of second couplers, each of said second couplers being coupled to said panel, each of said second couplers being spaced apart from each other and being distributed along said front edge of said panel, each of said second couplers being aligned with a respective one of said first couplers, each of said second couplers releasably engaging said respective first coupler when said pouch is folded onto itself thereby facilitating said pouch to enclose said plurality of beads;
a second mating member being coupled to said panel, said second mating member releasably engaging said first mating member for attaching said panel to said blanket, said second mating member extending along a full length of said front edge of said panel;
a plurality of vents, each of said vents being coupled to said panel wherein each of said vents is configured to pass air into said pouch thereby facilitating said beads to release the chemical scent from said pouch for purposes of aromatherapy;
a plurality of infusion lines, each of said infusion lines being integrated into said blanket, each of said infusion lines being comprised of a fluid absorbent material, each of said infusion lines being positioned between said top surface and said lower surface of said blanket, said plurality of infusion lines being arranged into an array in said blanket;
an input being coupled to said blanket, said input being in fluid communication with said plurality of infusion lines, said input being positioned on said top surface of said blanket, said input being positioned adjacent to said front side of said perimeter edge of said blanket; and
an infusion unit being removably attachable to said input such that said infusion unit is in fluid communication with said plurality of infusion lines, said infusion unit containing a liquid scent thereby facilitating each of said infusion lines to absorb the liquid scent wherein said infusion lines are configured to release the scent associated with the liquid scent from said blanket for the purposes of aromatherapy.

\* \* \* \* \*